United States Patent
Ben-Yosef et al.

(10) Patent No.: US 6,335,373 B1
(45) Date of Patent: Jan. 1, 2002

(54) PROCESS TO PRODUCE STABILIZED CARNOSIC ACID IN HIGH CONCENTRATION

(75) Inventors: Gil Ben-Yosef, Even Yehuda; Arkady Garbar, Yokneam, both of (IL)

(73) Assignee: Lycored Natural Products Industries, Ltd., Beer Sheva (IL)

( * ) Notice: Subject to any disclaimer, the term of this patent is extended or adjusted under 35 U.S.C. 154(b) by 0 days.

(21) Appl. No.: 09/403,099
(22) PCT Filed: Apr. 16, 1997
(86) PCT No.: PCT/IL97/00125
  § 371 Date: Jan. 18, 2000
  § 102(e) Date: Jan. 18, 2000
(87) PCT Pub. No.: WO98/46554
  PCT Pub. Date: Oct. 22, 1998
(51) Int. Cl.⁷ .............................. A01N 31/08; A61K 31/05
(52) U.S. Cl. .............................................. 514/732; 530/507
(58) Field of Search ............................................. 514/732

(56) References Cited

U.S. PATENT DOCUMENTS

| 2,124,706 A | 7/1938 | Maveety et al. |
| 4,012,531 A | 3/1977 | Viani |
| 4,363,823 A | 12/1982 | Kimura et al. |
| 4,450,047 A | 5/1984 | Malzahn |
| 4,450,097 A | 5/1984 | Nakatani et al. |
| 5,256,700 A | 10/1993 | Aeschbach et al. |
| 5,859,293 A | * 1/1999 | Bailey et al. .................. 562/467 |

FOREIGN PATENT DOCUMENTS

| EP | 0 582 318 | 2/1994 |
| WO | 93 06190 | 4/1993 |

* cited by examiner

Primary Examiner—Shep K. Rose
Assistant Examiner—Donna Jaque
(74) Attorney, Agent, or Firm—Browdy and Neimark

(57) ABSTRACT

A novel process for the production of the natural antioxidant, carnosic acid, by extracting it from rosemary leaves with an aqueous solution of a lower alkyl alcohol in the presence of a water soluble acid is described. The extraction of the carnosic acid is very selective, i.e. very few other chemicals such as pro-oxidants from the plant are extracted. Furthermore, a method for the stabilization of the extracted acid from decomposition and a method of preparing the acid in high concentration are described.

19 Claims, No Drawings

PROCESS TO PRODUCE STABILIZED CARNOSIC ACID IN HIGH CONCENTRATION

CROSS REFERENCE TO RELATED APPLICATION

The present application is the national stage under 35 U.S.C. 371 of PCT/IL97/00125, filed Apr. 16, 1997.

BACKGROUND OF THE INVENTION

The present invention describes an improved process for the extraction of an important biochemical, carnosic acid. The present invention more particularly describes an improved process for the extraction of carnosic acid from rosemary leaves a method of stabilizing the acid from decomposition and a method of preparing the acid in high concentration. Carnosic acid is characterized in its antioxidative function and is the most active ingredient in the prevention of the oxidation of fatty acids. The biochemical was found by Linde in 1962 to exist in *slavia officinalis* and by Wenkert in 1965 to exist in rosmarinus offinalis. Later the carnosic acid was found to exist also in other plants of the same family like *s. scanariesis, s. sclarea* and *s. triloban*. Carnosic acid is phenolic diterpene ($C_{20}H_{28}O_4$) identified by Brieskorn and Domling in 1964 to be very potent antioxidant. Its antibiotic action against stephilococus and dental caries was also reported.

Numerous methods for extracting carnosic acid are described in U.S. Pat. No. 5,256,700 whose contents are incorporated by their mention. Further processes are found in the following U.S. Pat. No. 2,124,706; 4,012,531; 4,363,823; and 4,450,047.

OBJECTIVES OF THE INVENTION

It is the objective of the present invention to provide a novel process to extract carnosic acid from rosemary leaves. It is also the objective of the invention to provide a novel process to extract carnosic acid from rosemary leaves which stabilizes the carnosic acid from decomposition. A further objective of the present invention is to provide a novel process which affords very high concentrations of carnosic acid.

SUMMARY OF THE INVENTION

In accordance with the present invention there is provided a novel process to extract carnosic acid from rosemary leaves comprising treating the rosemary leaves with an aqueous solution of a lower alkyl alcohol in the presence of a water soluble acid and further optionally purifying the carnosic acid via extraction

DETAIL DESCRIPTION OF THE INVENTION

The lower all alcohols found suitable for the present invention are chosen from the group consisting of methanol, ethanol, propanol, butanol, pentanol, and mixtures of these with ethanol preferred.

The lower alkyl alcohols are present in the extracting media in a concentration of 40% to 70% alcohol, preferably 55% to 65% alcohol, and most preferably 60% alcohol. The extraction using aqueous lower alkyl alcohols may be effected in one or more steps.

The water soluble acids found suitable for the present invention are selected from the group consisting of phosphoric acid and ascorbic acid, hydrochloric acid, acetic acid, citric acid and mixtures of these with phosphoric acid preferred. Said acids are present in a concentration of 0.1% to 30%, preferably 0.1 to 2%. The carnosic acid is removed from the aqueous alcoholic solutions by treating with vegetable oil, where almost any sort of vegetable alone or in combination with another vegetable oil can be used.

The carnosic acid dissolved in the vegetable oil may be further concentrated by extraction using a buffer of disodiumtetraborate at a pH range of 7.5 to 9.5, prefersbly 8.5 to 9.5 to afford carnosic acid in concentration of as high as 80% to 90%.

Examples 1,2,6 to 8 show the process of extracting with alkyl alcohol and the good yield obtained. Examples 3 to 5 are comparative Examples showing the lower yield obtained using other organic solvents.

Example 9 together with Table 1 shows the effect of the acid on the stability of the carnosic acid and the advantages of ascorbic acid and phosphoric acid, especially phosphoric acid.

Example 10 shows how the concentrations of carnosic acid may be increased through successive extraction in the presence of a buffer of disodiumtetraborate.

The present invention specifically describes the selective extraction of carnosic acid directly from the plant using an acidic polar solution containing water, lower alkyl alcohol and acid. The use of this particular extraction solution is very beneficial with regard to the following results: a) High yield of camosic acid in the concentrate. b) Extraction of the carnosic acid is very selective. Very few other chemicals such as pro-oxidants from the plant are extracted. c) Further oxidation of the carnosic acid to carnosol or in the extraction process is prevented. In addition the carnosic acid is stable for a period of more than 24 hours in this solution d) The high distribution coefficient of the extracting solution results is effective extraction process of carnosic acid. Following the extraction the carnosic acid moves to the apolar phase as a result of the change in the distribution coefficient of the solution as the alcohol is evaporated. Control of the alcohol concentration in the solution enables the undesirable fractions that will move to the polar phase. As an apolar phase one can use a non carnosic acid. Alternatively the polar phase can be some volatile solvent thus enabling the crystallization of the carnosic acid.

While the invention will now be described in connection with preferred embodiments in the following examples, it will be understood that it is not intended to limit the invention to these particular embodiments. On the contrary, it is intended to cover all alternatives, modifications and equivalents, as may be included within the scope of the preferred embodiments, will serve to illustrate the practice of this invention, it being understood that the particulars shown are way of example and for purposes of illustrative discussion of preferred what is believed to be the most useful and readily understood description of procedures, as well as of the principles and conceptual aspects of the invention.

EXAMPLES

Example 1

To 1.6 litre of ethanol (60%) containing 1% phosphoric acid are added 200 gr. of dried and finely ground rosemary leaves, having a concentration of 4.3% carnosic acid. Extraction is done for 3 hours at room temperature. 1.26 litre of extract are obtained by vacuum filtration of the biomass. 45 gr. of vegetable oil are added and of 0.86 litre alcohol evaporated. The two phases are separated and the residual water and alcohol present in the oil phase (ca. 30% alcohol) are removed by a vacuum pump resulting in 56 gr. of a brown liquid. Carnosic acid concentration is 10.3% and the overall yield of the process is 67.1%.

Example 2

To 1.6 litre of absolute ethanol containing 1% phosphoric acid are added 200 gr. of dried and finely ground rosemary leaves, having a concentration of 4.3% carnosic acid. Extraction is done for 3 hours at room temperature. 1.29 litre of extract are obtained by vaccum filtration of the biomass. 45 gr. of vegetable oil are added and the concentrate is evaporated. Residual solvent is removed by a vacuum pump so as to obtain 83.4 gr. of a viscous dark green paste. Carnosic acid concentration is 7.1% and the overall yield of the process is 68.6%.

Example 3

To 1.6 litre of Hexane are added 200 gr. of dried and finely ground rosemary leaves, having a concentration of 4.3% carnosic acid. Extraction is done for 3 hours at room temperature. 1.31 litre of extract are obtained by vacuum filtration of the biomass. 45 gr. of vegetable oil are added and the hexane is evaporated Residual solvent is removed by a vacuum pump so as to obtain 50.5 gr. of a dark green liquid. Carnosic acid concentration is 2.1% and the overall yield of the process is 12.5%.

Example 4

To 1.6 litre of Benzene are added 200 gr. of dried and finely ground rosemary leaves, having a concentration of 4.3% carnosic acid. Extraction is done for 3 hours at room temperature. 1.28 litre of extract are obtained by vacuum filtration of the biomass. 45 gr. of vegetable oil are added and the benzene is evaporated. Residual solvent is removed by a vacuum pump so as to obtain 54.6 gr. of a dark green liquid. Carnosic acid concentration is 2.8% and the overall yield of the process is 17.8%

Example 5

To 1.6 litre of Ethyl-acetate are added 200 gr. of dried and finely ground rosemary leaves, having a concentration of 4.3% carnosic acid. Extraction is done for 3 hours at room temperature. 1.24 litre of extract are obtained by vacuum filtration of the biomass. 45 gr. of vegetable oil are added and the ethyl-acetate is evaporated. Residual solvent is removed by a vacuum pump so as to obtain 71.3 gr. of a dark green viscous paste. Carnosic acid concentration is 8.5% and the overall yield of the process is 70.4%.

Example 6

To 1.6 litre of ethanol (73%) containing 1% phosphoric acid are added 200 gr. of dried and finely ground rosemary leaves, having a concentration of 4.3% carnosic acid. Extraction is done for 3 hours at room temperature. 1.28 litre of extract are obtained by vacuum filtration of the biomass. 45 gr. of vegetable oil are added and 1.1 litre alcohol is evaporated. The two phases are separated and the residual water and alcohol present in the oil phase (ca. 30% alcohol) are removed by a vacuum pump resulting in 62.2 gr. of a brown liquid. Carnosic acid concentration is 9.5% and the overall yield of the process is 68.7%.

Example 7

To 1.6 litre of ethanol (50%) containing 1% phosphoric acid are added 200 gr. of dried and finely ground rosemary leaves, having a concentration of 4.3% carnosic acid. Extraction is done for 3 hours at room temperature. 1.23 litre of extract are obtained by vacuum filtration of the biomass. 45 gr. of vegetable oil are added and 0.49 litre alcohol evaporated. The two phases are separated and the residual water and alcohol present in the oil phase (ca. 30% alcohol) are removed by a vacuum pump resulting in 53.1 gr. of a brown liquid. Carnosic acid concentration is 8.9% and the overall yield of the process is 54.9%.

Example 8

To 1.6 litre of ethanol (40%) containing 1% phosphoric acid are added 200 gr. of dried and finely ground rosemary leaves, having a concentration of 4.3% carnosic acid. Extraction is done for 3 hours at room temperature. 1.19 litre of extract are obtained by vacuum filtration of the biomass. 45 gr. of vegetable oil are added and 0.24 litre alcohol evaporated. The two phases are separated and the residual water and alcohol present in the oil phase (ca. 30% alcohol) are removed by a vacuum pump resulting in 49.2 gr. of a brown liquid. Carnosic acid concentration is 4.0% and the overall yield of the process is 22.9

Example 9

Stabilization of Carnosic Acid for a Period of More Than 24 Hours.

To 4.0 litre of ethanol (60%) are added 500 gr. of dried and finely ground rosemary leaves, having a concentration of 4.3% carnosic acid. Extraction is done for 3 hours at room temperature. 3.22 litre of extract are obtained by vacuum filtration of the biomass. The concentrate is divided to 200 ml. portions where different acids at various concentrations are added to these portions. All portions are kept in the dark and the variations in the carnosic acid concentrations of the different portions are checked. Table 1 shows the results where it is apparent that lack of acid results in a decrease of 50% carnosic acid. Only under acidic conditions is the concentration of carnosic acid retained where the optimal acids are phosphoric and ascorbic acid.

TABLE 1

THE EFFECT OF THE Ph ON THE CONCENTRATION OF CARNOSIC ACID

Concentration of Carnosic (mg/ml)

| Acid | Acid Concen % | Time Zero | +1 hour | +2 Hours | +5 Hours | +24 hour | +48 hours |
| --- | --- | --- | --- | --- | --- | --- | --- |
| Control | 0 | 4.8 | 4.51 | 4.42 | 4.27 | 3.55 | 2.78 |
| HCl | 0.1 | 4.8 | 4.72 | 4.68 | 4.52 | 3.69 | 2.93 |
| HCl | 1 | 4.8 | 4.78 | 4.72 | 4.53 | 4.54 | 4.39 |

TABLE 1-continued

THE EFFECT OF THE Ph ON THE CONCENTRATION OF CARNOSIC ACID

Concentration of Carnosic (mg/ml)

| Acid | Acid Concen % | Time Zero | +1 hour | +2 Hours | +5 Hours | +24 hour | +48 hours |
|---|---|---|---|---|---|---|---|
| HCI | 2 | 4.8 | 4.76 | 4.70 | 4.58 | 4.46 | 4.42 |
| Phosphoric | 1 | 4.8 | 4.82 | 4.79 | 4.76 | 4.78 | 4.79 |
| Phosphoric | 2 | 4.8 | 4.77 | 4.79 | 4.75 | 4.81 | 4.78 |
| Acetic | 1 | 4.8 | 4.76 | 4.77 | 4.74 | 4.59 | 4.26 |
| Acetic | 2 | 4.8 | 4.79 | 4.69 | 4.71 | 4.49 | 4.23 |
| Ascorbic | 0.05 | 4.8 | 4.75 | 4.71 | 4.68 | 4.78 | 4.79 |
| Ascorbic | 0.1 | 4.8 | 4.74 | 4.71 | 4.72 | 4.79 | 4.79 |
| Ascorbic | 0.5 | 4.8 | 4.86 | 4.83 | 4.82 | 4.81 | 4.82 |
| Ascorbic | 1 | 4.8 | 4.83 | 4.84 | 4.84 | 4.82 | 4.80 |
| Citric | 0.1 | 4.8 | 4.73 | 4.56 | 4.49 | 4.27 | 4.13 |
| Citric | 0.5 | 4.8 | 4.76 | 4.58 | 4.53 | 4.51 | 4.22 |
| Citric | 1 | 4.8 | 4.76 | 4.53 | 4.56 | 4.56 | 4.42 |

Exposure of carnosic acid in an extract when exposed to room temperature and light causes a marked decrease in a concentration of carnosic acid when the pH of the extract is above 6.

Example 10

Increasing the Concentration of Carnosic Acid 300 gr. a 5% Sodium bicarbonate solution (pH=8.16) is added to 100 gr. of a liquid product which contains 4.3% carnosic acid as obtained from the initial extractions of rosemary leaves and stirred for 10 minutes. The phases are separated, and the water phase is discharged. The material is extracted from the oil phase with 300 gr. of 0.01 disodiumtetraborate buffer (pH=9.18) for 20 min.: and the layers are separated. The aqueous phase pH is lowered from 7.96 to 1.5 by adding HCl. The precipitate obtained is filtered, air dried under 40° C. resulting in a 0.59 gr of dried precipitate containing 70% carnosic acid. To the remaining oil phase 300 gr of 0.01M disodium tetraborate buffer (pH=9.18) is added and the solution is stirred for 20 min. Phases are separated, where the pH of the aqueous phase is lowered from 7.93 to 1.52 by adding HCl. The precipitate obtained is filtered, air dried under 40° C. resulting in an additional 1.29 gr of dried precipitate containing 80% of carnosic acid. To the remaining oil phase 300 gr. of 0.01M disodium tetraborate buffer (pH=9.18) is added and the solution is stirred for 20 min. Phases are separated, where the pH of the aqueous phase is lowered from 8.08 to 1.5–2 by adding HCl. The precipitate obtained is filtered, air dried under 40° C. resulting in a 1.39 gr of dried precipitate containing 89% carnosic acid. To the oil phase previously extracted three times are added 0.01M disodium tetraborate buffer (pH=9.18) and the solution is stirred for 20 min. Phases are separated where the pH of the aqueous solution is lowered from 8.68 to 1.5 by adding HCl and an oil precipitate is obtained. Yield of carnosic acid is 65%.

We claim:

1. A process for producing carnosic acid from rosemary leaves, comprising treating said rosemary leaves with an aqueous solution of about 40%–75% of a lower alkyl alcohol, said aqueous solution further comprising a water soluble acid.

2. A process in accordance with claim 1 wherein the lower alkyl alcohol is selected from the group consisting of methanol, ethanol, propanol, pentanol and mixtures thereof.

3. A process in accordance with claim 1 wherein the lower alkyl alcohol is ethanol.

4. A process in accordance with claim 1 wherein the lower alkyl alcohol is present in the aqueous solution in a concentration of about 40%–70%.

5. A process according to claim 4 wherein the lower alkyl alcohol is present in the aqueous solution in a concentration of about 60%.

6. A process in accordance with claim 2 wherein the lower alkyl alcohol is present in the aqueous solution in a concentration of about 60%.

7. A process in accordance with claim 1 wherein the water soluble acid is selected from the group consisting of phosphoric acid, ascorbic acid, hydrochloric acid, acetic acid, citric acid and mixtures thereof.

8. A process in accordance with claim 7 wherein the water soluble acid is phosphoric acid.

9. A process in accordance with claim 1 wherein the acid is present in the aqueous solution in a concentration of about 0.1% to 30%.

10. A process in accordance with claim 1 wherein the acid is present in the aqueous solution in a concentration of about 0.1% to 2%.

11. A process in accordance with claim 1, wherein said treating is a single extraction step with said aqueous solution.

12. A process in accordance with claim 1 wherein said treating comprises a plurality of extraction steps with said aqueous solution in multiple stages.

13. A process for extracting carnosic acid from rosemary leaves comprising treating the rosemary leaves with an aqueous solution containing 55% to 65% ethyl alcohol in the presence of 0.19% to 2% phosphoric acid.

14. A process in accordance with claim 1 wherein the resulting solution of carnosic acid is initially treated with an aqueous bicarbonate solution and the extracting the resulting oil phase with an aqueous buffer solution of disodiumtetraborate.

15. A process in accordance with claim 14 wherein the pH of the buffer solution is in the range of 7.5 to 9.5.

16. A process in accordance with claim 14 wherein the pH of the buffer solution is in the range of 8.5 to 9.5.

17. A process in accordance with claim 14 wherein the oil phase acid is extracted with four separate portions of aqueous disodiumtetraborate solution.

18. A process in accordance with claim 14 wherein the oil phase acid is extracted with four separate portions of aqueous buffer solution.

19. A process according to claim 1 comprising the following stages:
   a) contacting the rosemary leaves with said aqueous solution;
   b) separating the solid phase which contains the leaves from the aqueous solution to obtain an aqueous phase;
   c) mixing oil into aqueous phase;
   d) removing the alcohol from the mixture obtained in stage c;
   e) separating the oil and aqueous phases to obtain an oil phase containing carnosic acid.

* * * * *